US 10,737,195 B2

(12) United States Patent
Brown et al.

(10) Patent No.: US 10,737,195 B2
(45) Date of Patent: Aug. 11, 2020

(54) CHEMICAL RECOVERY BY DISTILLATION OF DILUTE AQUEOUS SOLUTIONS PRODUCED IN ADVANCED BIO-FUELS PROCESSES

(71) Applicants: Christopher J. Brown, Amherst, NY (US); Charles C. Cromwell, West Seneca, NY (US); Christopher A. Spengler, Williamsville, NY (US)

(72) Inventors: Christopher J. Brown, Amherst, NY (US); Charles C. Cromwell, West Seneca, NY (US); Christopher A. Spengler, Williamsville, NY (US)

(73) Assignee: RCM Technologies (USA), Inc., Pennsauken, NJ (US)

( * ) Notice: Subject to any disclaimer, the term of this patent is extended or adjusted under 35 U.S.C. 154(b) by 0 days.

(21) Appl. No.: 15/935,433

(22) Filed: Mar. 26, 2018

(65) Prior Publication Data

US 2018/0290073 A1   Oct. 11, 2018

Related U.S. Application Data

(60) Provisional application No. 62/481,983, filed on Apr. 5, 2017.

(51) Int. Cl.
*B01D 3/14* (2006.01)
*B01D 3/32* (2006.01)
(Continued)

(52) U.S. Cl.
CPC .......... *B01D 3/146* (2013.01); *B01D 1/2856* (2013.01); *B01D 3/002* (2013.01); *B01D 3/143* (2013.01);
(Continued)

(58) Field of Classification Search
CPC ........ B01D 3/002; B01D 3/143; B01D 3/146; B01D 3/322; B01D 1/2856; B01D 53/261; C07C 29/80
See application file for complete search history.

(56) References Cited

U.S. PATENT DOCUMENTS

| 4,539,076 | A |   | 9/1985 | Swain |
| 4,566,947 | A | * | 1/1986 | Tsuruta ................ B01D 1/2856 |
|           |   |   |        | 203/14 |

(Continued)

FOREIGN PATENT DOCUMENTS

WO            053342          3/2017

OTHER PUBLICATIONS

International Search Report and Written Opinion of corresponding Application No. PCT/US2018/024307 dated Jun. 15, 2018.

*Primary Examiner* — Brian A McCaig
(74) *Attorney, Agent, or Firm* — Bond, Schoeneck & King, PLLC; Joseph Noto (57) ABSTRACT

A system and method for producing substantially anhydrous ethanol, methanol or other volatile chemicals includes: (a) a first distillation stripping column or column set with overhead vapors compressed using mechanical vapor recompression to strip off a weak ethanol overheads; (b) a second distillation rectifying column having a higher operating temperature than the stripping column; (c) a dehydration means in fluid communication with the rectifying column; (d) reboiler for the stripping column which partially condenses the vapor from the mechanical vapor recompression, (e) a trim condenser which completes the condensing of the vapor/liquid mix of the reboiler, (f) a heat recovery circuit which condenses the rectifying column overheads and molecular sieve dry ethanol condenser and (g) a heat (Continued)

exchange to transfer the recovered heat of (f) to the first distillation stripping column reboiler feed.

25 Claims, 9 Drawing Sheets

(51) Int. Cl.
*C07C 29/80* (2006.01)
*B01D 53/26* (2006.01)
*B01D 1/28* (2006.01)
*B01D 3/00* (2006.01)

(52) U.S. Cl.
CPC ........... *B01D 3/322* (2013.01); *B01D 53/261* (2013.01); *C07C 29/80* (2013.01); *Y02P 20/124* (2015.11); *Y02P 20/57* (2015.11); *Y02P 70/34* (2015.11)

(56) References Cited

U.S. PATENT DOCUMENTS

| | | |
|---|---|---|
| 7,981,256 B2 | 7/2011 | Wegerer et al. |
| 9,000,237 B2 | 4/2015 | Powell |
| 2017/0036139 A1 | 2/2017 | Lee |
| 2017/0348607 A1* | 12/2017 | Crawford ............ B01D 1/0058 |

* cited by examiner

CHEMICAL RECOVERY BY DISTILLATION OF DILUTE AQUEOUS SOLUTIONS PRODUCED IN ADVANCED BIO-FUELS PROCESSES

CROSS REFERENCE

This application claims the benefit of the filing date of U.S. Provisional Patent Application Ser. No. 62/481,983, filed Apr. 5, 2017, which is hereby incorporated by reference in its entirety.

FIELD

The present disclosure relates to systems and methods for chemical recovery by distillation of dilute aqueous solutions, and in particular of dilute aqueous solutions produced in advanced bio-fuels processes.

BACKGROUND

Ethanol production from grains, primarily corn, has grown rapidly from the late 1990's through today with much of that growth occurring between 2004 and 2009 now culminating in a national production of over 16 billion gallons per year in 2016. The U.S. Renewable Fuels Standard (RFS2) calls for production of 15 billion gallons per year in conventional biofuels (grain based ethanol) starting in 2015 forward. It also specifies increasing amounts from cellulosic sources from current levels to over 15 billion gallons per year by 2022. This will be a very difficult achievement unless advanced technologies for biomass conversion are teamed up with innovative means to recover fuel ethanol and other bio-fuels. These innovations must make the best use of the conversion streams for added value products as well as process these streams with limited energy input.

Internationally, there are similar goals to increase alternative biomass conversion to fuels and such aggressive growth plans will require government support and private equity investment. Both will only be possible if the supported technologies are economically viable and sustainable.

World supplies and availability of crude oil are not limitless although recent years have revealed still new accessible pools of fossil fuels. Developing economies often have limited local natural resources and underdeveloped distribution channels for energy products. These factors create considerable incentive for the development and use of alternative fuels as well as production of the same in remote locations making use of regionally available biomass, particularly that which must be landfilled or burned openly. Furthermore, environmental concerns have required use of additives which aid in oxygenation of the motor fuels. These additives have created concerns of their own for environmental damage. Ethanol has established wide popularity as a fuel additive capable of addressing these concerns, particularly when mixed with gasoline to form a mixture known as gasohol. Gasohol may contain up to about 10 vol. % ethanol and could be permitted in amounts up to 15 vol. %, without modifications to presently designed automobile engines being required, thereby extending the volume of motor fuel availability by a like percentage.

The current major source of the ethanol used in gasohol is derived primarily from the fermentation of mash, usually from corn or wheat or other grain. Natural fermentation is able to produce an ethanol-water product mixture containing, at most, about 12 wt % to 15.5 wt % ethanol. This mixture may easily be concentrated by distillation to about 91% to 95% ethanol. Higher concentrations of ethanol, however, as required in gasohol are obtained only by expenditures of great amounts of energy and great difficulty due to the formation of an ethanol-water azeotrope at about the 95% ethanol concentration. A means of achieving greater than 95% ethanol concentration without 1) such a great expenditure of energy or 2) loss of the used energy is thus extremely valuable. Such schemes have been employed in the past to recover heat from azeotropic distillation employing tertiary entrainers such as benzene (U.S. Pat. Nos. 4,372,822, 4,422,903 and 5,035,776). Others earlier had considered the option of using heat from the stripping/rectifying column to heat an azeotropic distillation (U.S. Pat. Nos. 1,860,554 and 4,217,178). Additionally, one invention considered generating steam from the heat in overhead vapors of the azeotropic distillation (U.S. Pat. No. 4,161,429) and another used mechanical vapor recompression of the overhead vapors to recover heat in the fashion of a heat pump for heating the azeotropic distillation column(s) (U.S. Pat. No. 5,294,304). Since about 1998 the prevalent approach to producing ~99.5 wt % ethanol from the 91 to 95% distillation overheads is the use of pressure vacuum swing adsorption (PVSA) on a 3A Zeolite media. Several effective methods of implementing this process have been proposed and employed. One of these is U.S. Pat. No. 9,308,489 B2, "Adsorption Process for the Dehydration of Alcohol".

Further discussion regarding advances in grain based ethanol production and integration of the distillation, evaporation, and dehydration units of operation can be found on U.S. Pat. No. 7,867,365 B2 "Ethanol Distillation with Distillers Soluble Solids Recovery Apparatus.

The recovery of bio-fuels, chemicals, and volatiles such as ethanol and methanol from developing biomass conversion processes and cellulosic conversion processes is made more challenging since many of these processes result in an aqueous stream of dilute bio-fuel and or chemicals. Many of these processes require large quantities of water and the resulting sugar solution for fermentation is dilute resulting in low ethanol, methanol, or other bio-fuel/chemical concentration. Conversion of cellulose and hemicellulose in biomass results in a mixture of six carbon and five carbon sugars which limits the final ethanol concentration that yeast can produce. For some biomass conversions a gaseous mix may be produced and directly metabolized by yeast, algae, or other organisms to produce chemicals, ethanol, methanol, butanol, or many other compounds specific to the organism's metabolic pathways. These gaseous mixes can be a synthesis gas, exhaust flue gas rich in carbon dioxide, carbon dioxide from traditional dry mill fuel ethanol production, or any number of other sources emitting carbon dioxide.

Recovering these chemicals including ethanol from dilute solutions can be prohibitively energy intensive. Some processes for recovery require low temperature operation to maintain the viability of the microorganism producing the chemical weak feed stream. Some can operate at higher temperatures where the biologicals have been removed by other means. For all, the very high concentration of water requires innovative approaches to limit energy consumption and maximize the recovery of valuable chemicals and fuels. This invention is intended to solve this energy problem.

SUMMARY

In accordance with one aspect of the present disclosure, there is provided a method for energy efficient distillation of weak feed steams of volatile components including the steps of:

(a) providing a weak feed stream of low concentration volatile components to a first distillation stripping column;

(b) distilling the weak stream feed in the first distillation stripping column to form a higher strength overhead product vapor stream and directly supplying the higher strength overhead product vapor stream to a vapor compression means to produce a higher pressure vapor;

(c) partially condensing the higher pressure vapor in a first distillation stripping column reboiler, partially vaporizing a bottom liquid product from the first distillation stripping column in the first distillation stripping column reboiler and providing a bottom vapor stream to the first distillation stripping column to strip volatile compounds or chemicals from the weak stream feed;

(d) completing in a trim condenser the condensing of the higher pressure vapor which has been partially condensed in the first distillation stripping column reboiler to recover a higher strength condensed overhead stream which is the condensed higher strength overhead product vapor stream of the first distillation stripping column;

(e) distilling the higher strength condensed overhead product stream in a second higher pressure distillation column to produce a high strength product stream in the second higher pressure distillation column overheads; and (f) recovering heat from an external source to add to the first distillation stripping column reboiler.

In accordance with another aspect of the present disclosure, there is provided a method for energy efficient distillation of feed steams of weak of volatile components while limiting the pressure loss in the system by parallel flow of vapor in the distillation operation including the steps of:

(a) providing a feed stream of weak volatile components to a series of distillation stripping columns, the first distillation stripping column in the series receiving the feed stream of weak volatile components, each of the other distillation stripping columns in the series in succession receiving the bottom stream from the prior distillation stripping column in the series, and each distillation stripping column in the series having a reboiler which partially condenses compressed overhead vapor from the series of distillation stripping columns, the reboilers each partially vaporizing a weak volatile stream from the final distillation stripping column in the series or using an intermediate process water feed as well as sequentially reducing the weak volatile components of the feed stream while vapor from each of the reboilers flows to the associated distillation stripping column in the series;

(b) distilling the feed stream of weak volatile components in the series of distillation stripping columns to form a higher strength overhead product vapor stream which flows at the same overhead pressure directly supplying a vapor compression means raising the lower pressure of the overhead vapor to produce a higher pressure vapor at an operating pressure of a heated side of the reboilers;

(c) partially condensing the higher pressure vapor in the reboilers, partially vaporizing a bottom liquid product from the series of distillation stripping columns and providing a bottom vapor stream to the associated distillation stripping columns to strip volatile compounds or chemicals from the weak feed stream;

(d) completing in a trim condenser the condensing of the higher pressure vapor which has been partially condensed in the reboilers to recover a higher strength condensed overhead stream which is the condensed higher strength overhead product vapor stream of the series of distillation stripping columns;

(e) distilling the higher strength condensed overhead product stream in a second higher pressure distillation column to produce a high strength product stream in the second higher pressure distillation column overheads; and recovering heat from an external source to add to the reboilers.

In accordance with another aspect of the present disclosure, there is provided a method for processing a weak feed stream, including:

stripping the weak feed stream of volatile components in a first stripping column forming an overhead vapor;

compressing the overhead vapor in a compression step to produce a higher pressure vapor;

partially condensing the higher pressure vapor in a first stripping column reboiler;

further condensing the partially condensed higher pressure vapor in a trim condenser to form a condensate;

distilling the condensate from the trim condenser in a higher pressure distillation system; and providing heat from the condensate distillation to an auxiliary heater or reboiler of the first stripping column.

These and other aspects of the present disclosure will become apparent upon a review of the following detailed description and the claims appended thereto.

DETAILED DESCRIPTION

The present disclosure relates to a system and method for producing ethanol, methanol, or other volatile chemicals from a cellulosic or other biomass conversion source or other biological or chemical source and that operates to purify and dry the ethanol, methanol, or other volatile chemical from the source, which is referred to herein as "feed source", produced by the conversion process. An embodiment of a system for producing substantially anhydrous ethanol, methanol or other volatile chemicals includes: (a) a first distillation stripping column or column set with overhead vapors compressed using mechanical vapor recompression (e.g., turbofans or centrifugal compressor) to strip off a weak ethanol overheads; (b) a second distillation rectifying column having a higher operating temperature than the stripping column; (c) a molecular sieve dehydration means in fluid communication with the rectifying column; (d) reboiler for the stripping column which partially condenses the vapor from the mechanical vapor recompression, (e) a trim condenser which completes the condensing of the vapor/liquid mix of the reboiler, (f) a heat recovery circuit which condenses the rectifying column overheads and molecular sieve dry ethanol condenser and (g) a heat exchange to transfer the recovered heat of (f) to the first distillation stripping column reboiler feed.

Mechanical vapor recompression is a well-known approach to compress lower pressure vapor so that it can be condensed at higher pressure and effect the evaporation or boiling of a lower pressure liquid. For evaporation, the overhead vapor of the evaporator is compressed and then condensed in the shell of the evaporator accomplishing the boiling or evaporation of the evaporator in a closed loop recovering the latent heat of the evaporator as a heating steam for the evaporator. Similarly for distillation, the overhead vapor can be compressed so that it can be condensed in the reboiler and the reboiler provides a lower pressure vapor for operation of the distillation column.

The challenge for distillation is to limit the amount of compression and fully condense the overhead vapor. For example, an overhead vapor of 20 wt % ethanol at 2 psia will start condensing at 124° F. and complete condensing at close to 100° F. A compressor to produce the 2 psia vapor can take an overhead at 0.95 psia from distillation for which the bottoms is at 1.1 psia and 105° F. and the reboiler must then operate at 105° F. The recovered compressed vapor heat can only be partially condensed under these conditions. In an embodiment, a solution is to use heat from further distillation of the weak condensed overhead to supplement the compressed vapor and then complete the condensing of the compressed overhead vapor in a trim condenser. See FIG. 1, a flow sketch "Split Condensing Range Concept", and three sets of vapor condensing curves and ranges FIGS. 2, 3, and 4.

Another challenge of mechanical vapor recompression distillation is overcoming the pressure drop in the stripping column so that most of the compression of the vapor is recovered as usable heat. In an embodiment, a multi-stage system using several columns or column sections connected in series for the "weak feed stream" flow and for each of these stages ethanol (other chemicals) are stripped in succession while these same columns/column sections are connected in parallel for the vapor flowing through them and to the compressor (MVR). The compressed vapors are then condensed in a series of reboilers which form another series of separations stages each removing more ethanol (other chemicals) at each stage. The weak feed stream feed from the columns feeding the first reboiler and each reboiler in succession is preheated and partially boiled in a preheater recovering heat form the final distilling part of the process. This embodiment is shown in the flow sketch of FIG. 5, "Series Liquid & Parallel Vapor Flow Concept".

Figure 1:
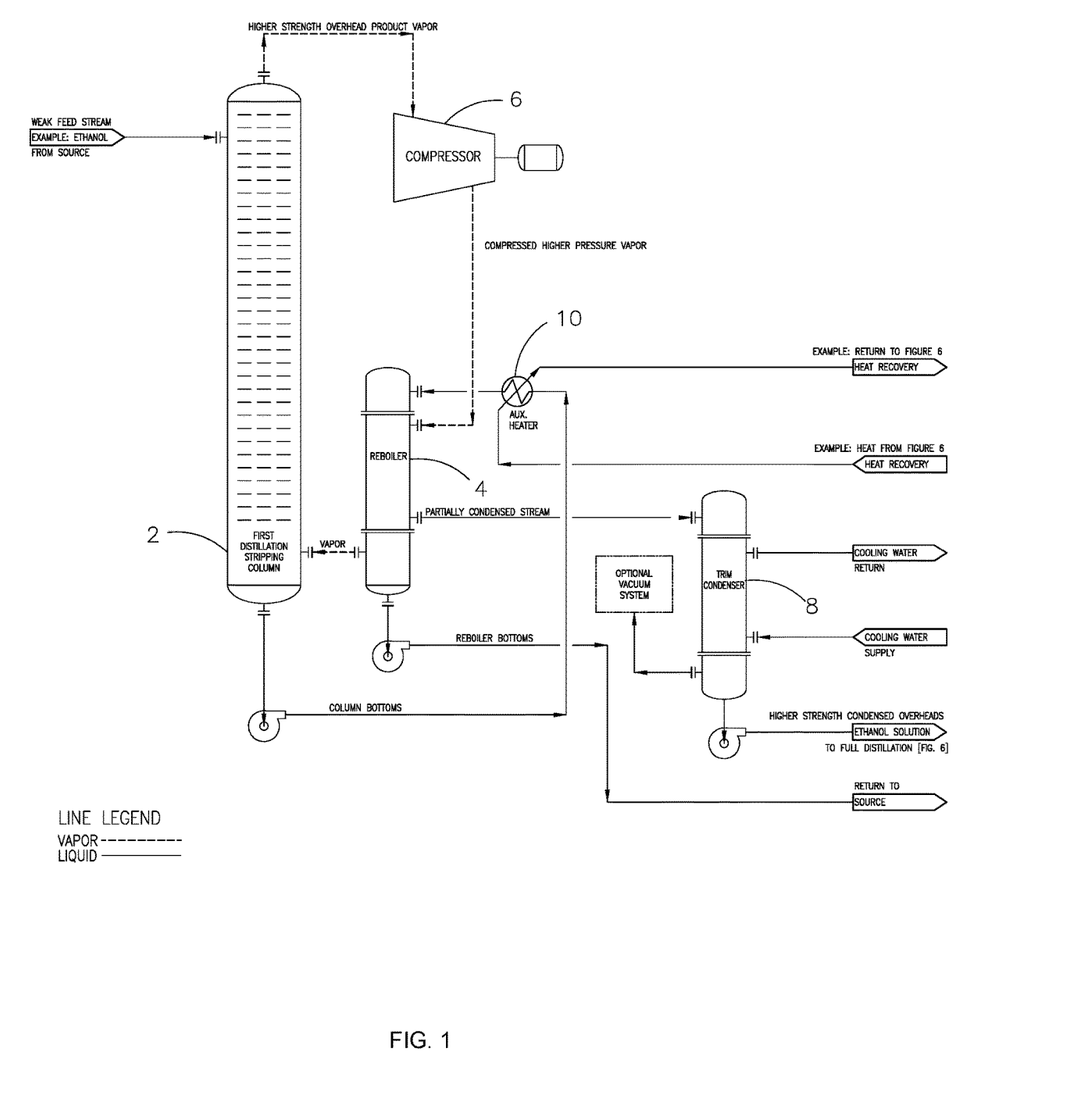
FIG. 1 is a schematic representation of a split condensing range concept in accordance with an embodiment of the present disclosure.

FIG. 1 illustrates an embodiment of a Split Condensing Range concept in one example of its application. The process equipment shown includes a distillation column 2, reboiler 4, compressor 6, trim condenser 8, and an auxiliary heater 10. A weak, for example ethanol, feed stream (can be other low concentration volatile chemical) enters the distillation column 2. The stream flows down through a plurality of stages (e.g., trays, packing, etc.) of the distillation column 2 while vapor from the reboiler 4 flows up the distillation column 2 contacting the liquid at each stage, the action of which sends the more volatile chemical (ethanol) up with the vapor depleting the feed stream of volatile components while increasing the concentration of volatile components in the vapor stream. The overhead vapor exiting the top of the distillation column 2 flows to a compressor 6 which increases the pressure of the vapor sufficiently above the distillation column 2 pressure that the compressed vapor can be used to heat the reboiler 4. The compressor 6 may be a high speed centrifugal compressor, turbofan, or other gas compression device. The auxiliary heater 10 provides additional heat from an external source to the reboiler 4 by heating the bottom liquid product from the distillation column 2. The reboiler 4 partially condenses the overhead compressed vapor to achieve an economical level of heat recovery. The higher volatile concentration of the compressed vapor condenses in the reboiler 4 providing heat to the reboiler 4 by release of the vapor's latent heat.

Figure 2:
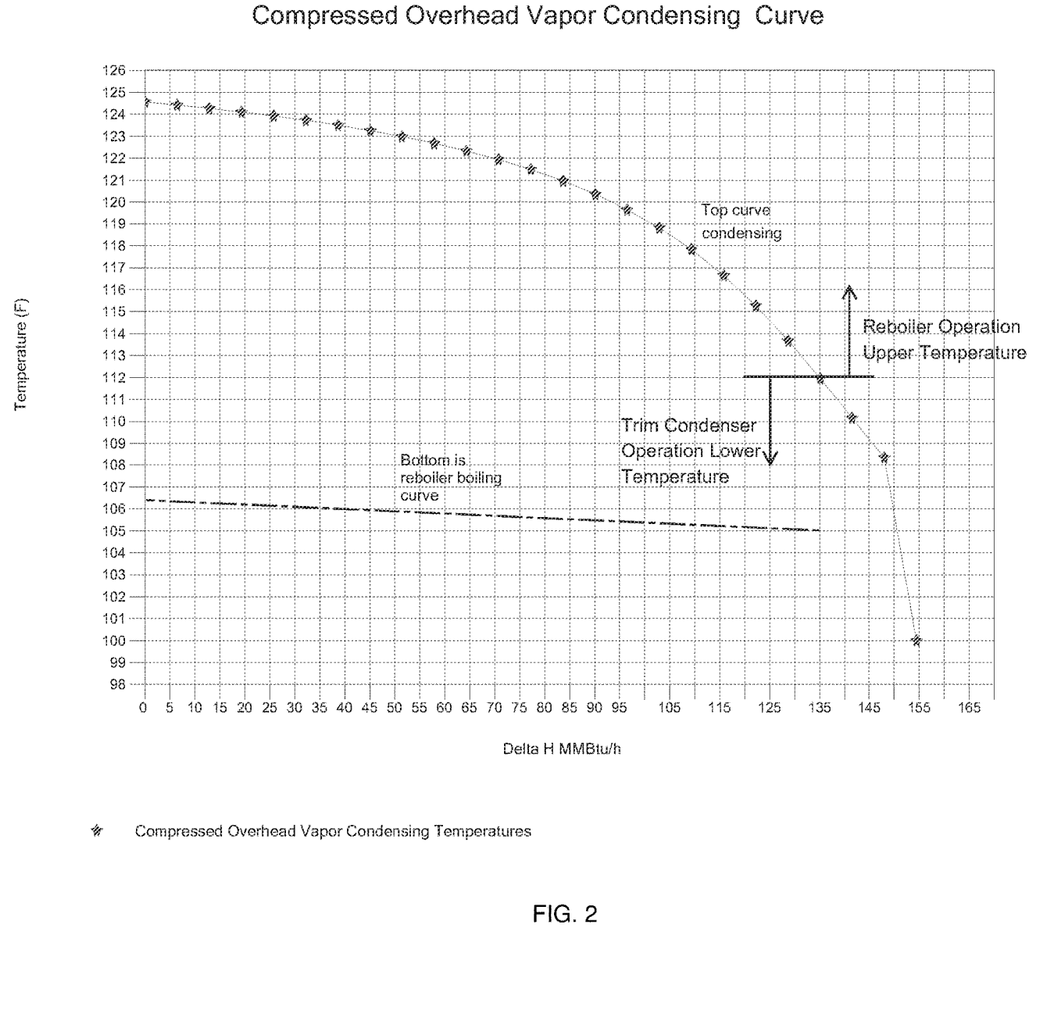
FIG. 2 shows a compressed overhead vapor condensing curve in accordance with an embodiment of the present disclosure.

FIG. 2, Compressor Exhaust Vapor Condensing Curve shows an example of the reboiler performance operation. Compressed vapor condenses over a wide condensing temperature range starting at 124.3° F. in this example and final condensing below 106° F. as shown by the top curve in FIG. 2. The boiling range of the reboiler, also shown by the bottom curve in FIG. 2, is 105° F. to 106.3° F. The full condensing range of the compressed vapor could not be condensed even with an infinite amount of surface area in the reboiler. The surface area of the reboiler, A, is equal to the heat load Q divided by the average temperature difference between the vapor and the boiling liquid times a heat transfer coefficient.

$$A=Q/(U \times dT)dT \to 0, A \to \infty$$

Figure 3:
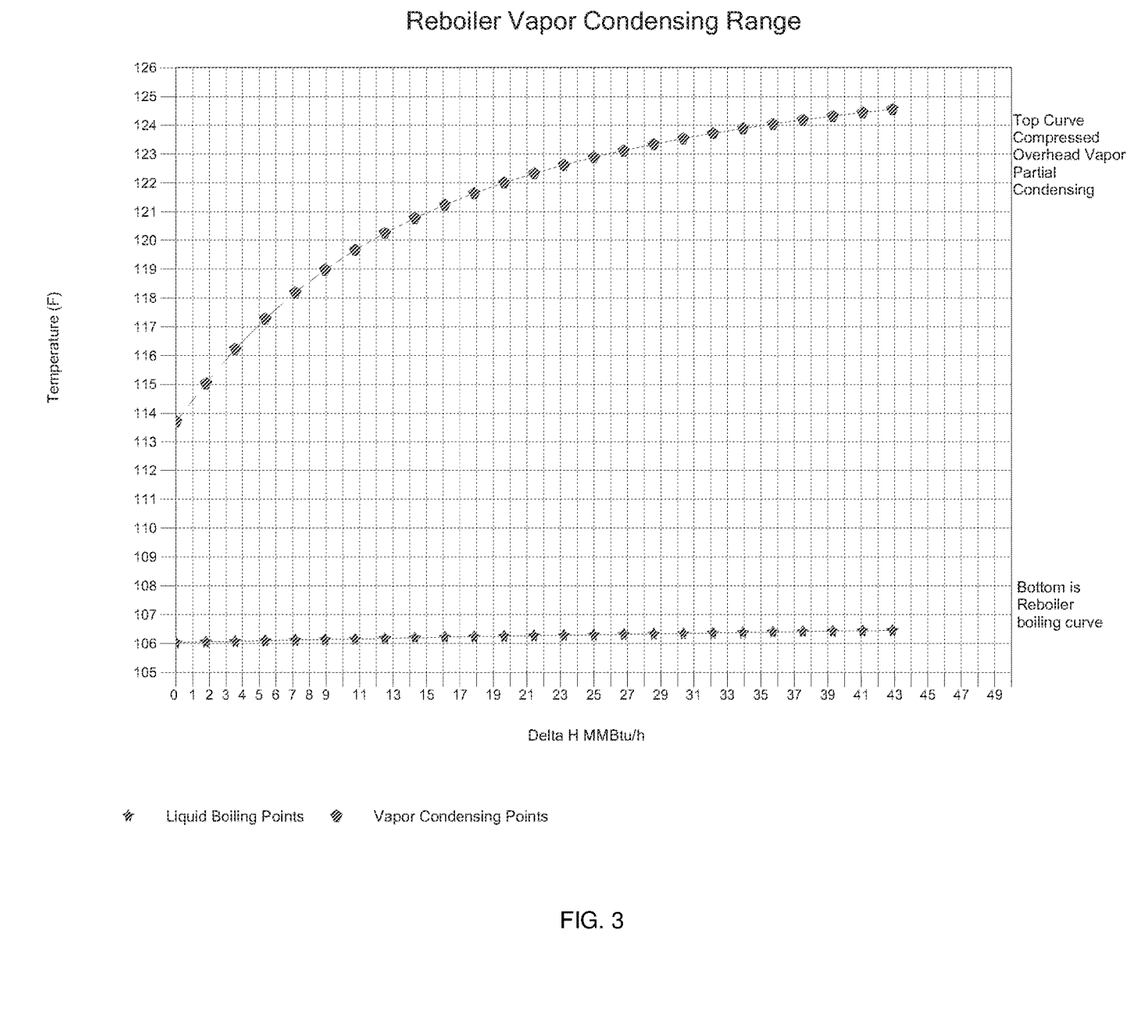
FIG. 3 shows a reboiler vapor condensing range in accordance with an embodiment of the present disclosure.
Figure 4:
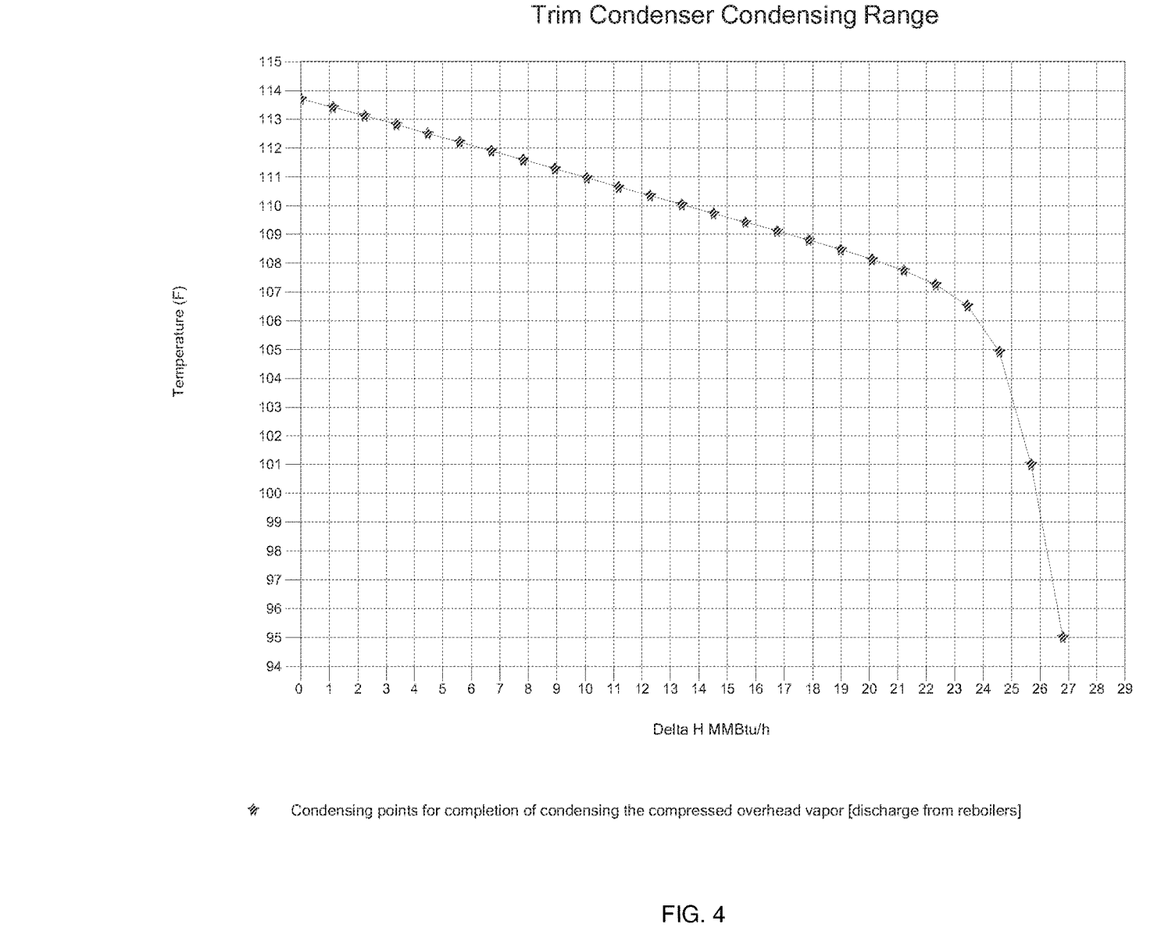
FIG. 4 shows a trim condenser condensing range in accordance with an embodiment of the present disclosure.

In this case the average temperature difference approaches zero and any real value divided by zero approaches infinity. This is not a practical result. One feature of this disclosure is to stop the condensing above the temperature of the boiling liquid in the reboiler and recover less than 100% of the compressed vapor's heating value then to send the partially condensed compressed vapor to the trim condenser which is cooled with an external cooling water or other coolant. FIG. 3 shows an example of the temperature profiles for the reboiler in a practical design as proposed in this disclosure. The top curve represents the vapor condensing points of the compressed overhead vapor partial condensing. The bottom curve represents the liquid boiling points of the reboiler boiling curve. FIG. 4 shows an example of a curve of the condensing points for completion of condensing the compressed overhead vapor discharge from reboilers for the condensing range for the trim condenser.

The total heat balance for the distillation is approximately equal to the heat leaving in the overhead vapor plus the heat leaving in the reboiler bottoms less the heat of the vapor from the reboiler less the heat of the feed stream:

$$Q_{Overhead}+Q_{Col\ Bottoms}-Q_{Feed}-Q_{Reboiler\ Vapor}=0$$

The reboiler heat balance is equal to the heat of the vapor from the reboiler plus the heat of the partially condensed stream plus the heat of the reboiler bottoms less the heat of the heated column bottoms entering the reboiler less the compressed overhead vapor from the compressor:

$$Q_{RB\ Vapor}+Q_{Partial\ Cond\ Stream}+Q_{RB\ Bottoms}-Q_{Heated\ Col\ Bottoms}-Q_{Compressed\ Overhead\ Vapor}=0$$

Generally, as shown for example in FIG. 1, the auxiliary heater 10 is recovering heat from an external source to make up for heat loss in the partially condensed stream sent to the trim condenser 8 and not used from the compressed overhead vapor for the distillation column 2 which allows a practical use of the compressed overhead vapor heat value. The external source for the auxiliary heater 10 can be from a higher pressure distillation of the condensed compressed overhead vapor to recover a purified ethanol product for which FIG. 6 is an example discussed further below.

Figure 5:
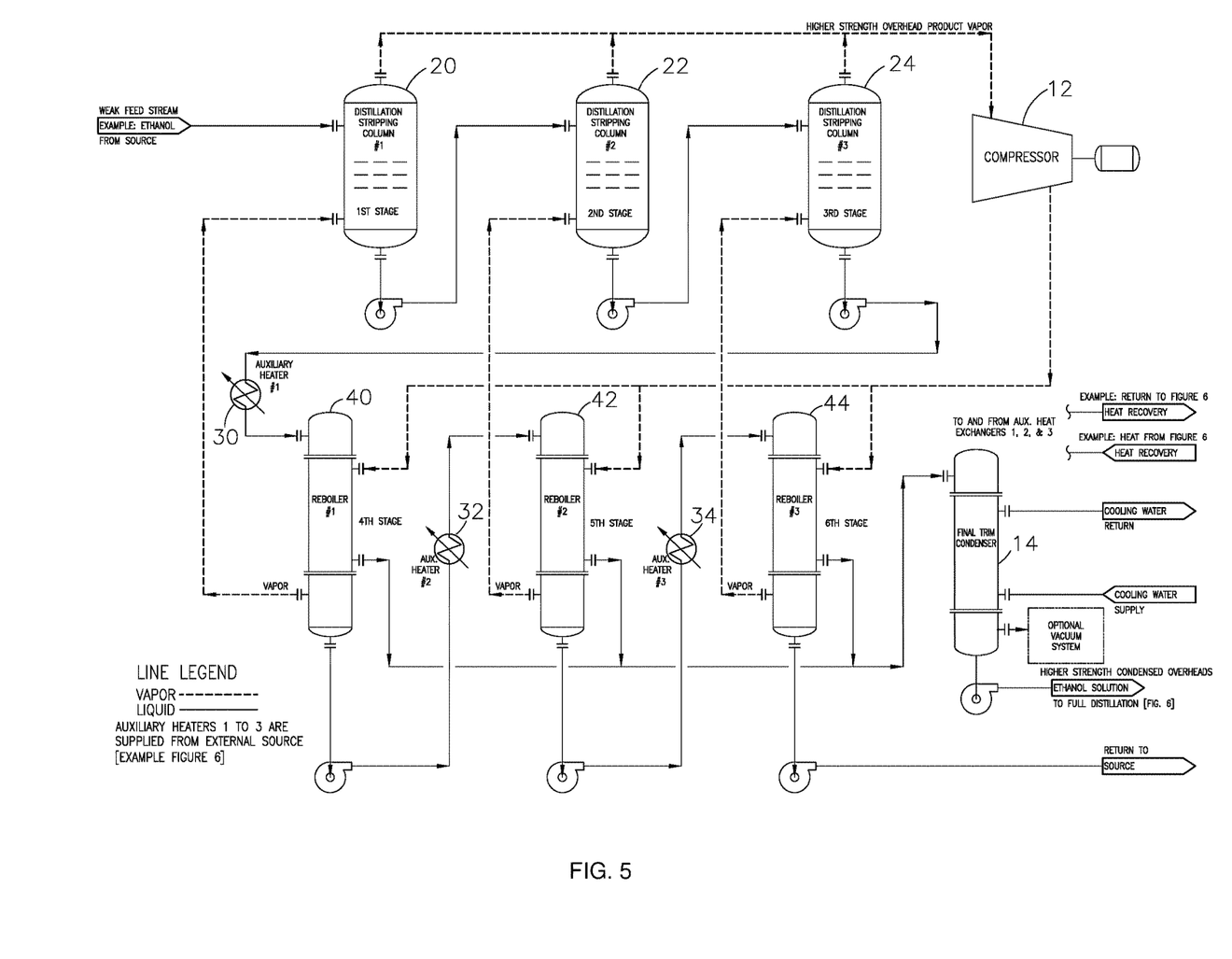
FIG. 5 is a schematic representation of a series liquid and parallel flow concept in accordance with an embodiment of the present disclosure.

FIG. 5 is an example of a Multi-Stage Parallel Vapor Flow Distillation concept for an embodiment of this disclosure, which reduces the pressure drop through the distillation process shown in FIG. 1 to allow for more effective use of the compressor's vapor compression power. This reduces pressure loss in distillation such that more of the temperature increase from the vapor compression can be utilized in the reboiler(s) maximizing the available heat of condensing the compressed overhead vapors. As shown in FIG. 5, weak ethanol feed, for example, enters three distillation sections 20, 22 and 24 in series to a $1^{st}$ stage of separation then to a $2^{nd}$ stage of separation, and then to a $3^{rd}$ stage of separation. At each of these three stages of separation the weak ethanol feed successively becomes more depleted of ethanol content before this stream is sent to the $1^{st}$ reboiler 40. After the weak ethanol feed stream leaves the $3^{rd}$ distillation stage of separation it flows in series to the $1^{st}$ reboiler 40, then a $2^{nd}$ reboiler 42, and then to a $3^{rd}$ reboiler 44. In each reboiler the weak ethanol feed stream is partially vaporized from heat supplied by auxiliary heaters 30, 32 and 34 and partially condensed compressed overhead vapor. This partial vaporization completes the depletion of ethanol in the weak ethanol feed stream so that essentially ethanol free or mostly ethanol free stripped feed is returned to the fermentation or other bio-reaction or similar front end processing source which is used to produce the weak ethanol feed stream. The vapor phase flow circuit is circulated in parallel with vapor from the three reboilers 40, 42 and 44 flowing to each of the three distillation sections 20, 22 and 24 providing stripping vapor to remove ethanol from the weak ethanol feed stream. The overhead vapor from the three distillation sections 20, 22 and 24 flows to a compressor 12 to compress the vapor for use in heating the reboilers 40, 42 and 44. The compressed overhead vapor is partially condensed in the reboilers 40, 42 and 44 similar to the manner discussed for FIG. 1 with the partially condensed streams flowing to a final trim condenser 14. Auxiliary heaters 30, 32 and 34 using an external heating source adds heating to the reboilers 40, 42 and 44 making up for heat not recovered from the compressed overhead vapors. The pressure drop for the vapor circuit is composed of pressure losses in flowing through the three distillation sections 20, 22 and 24 in parallel, pressure losses in the piping, and pressure losses flowing through the reboilers 40, 42 and 44 in series. This pressure drop is considerably less than that flowing through a single multi-stage distillation column and provides a more effective use of the compressed vapor.

Figure 6:
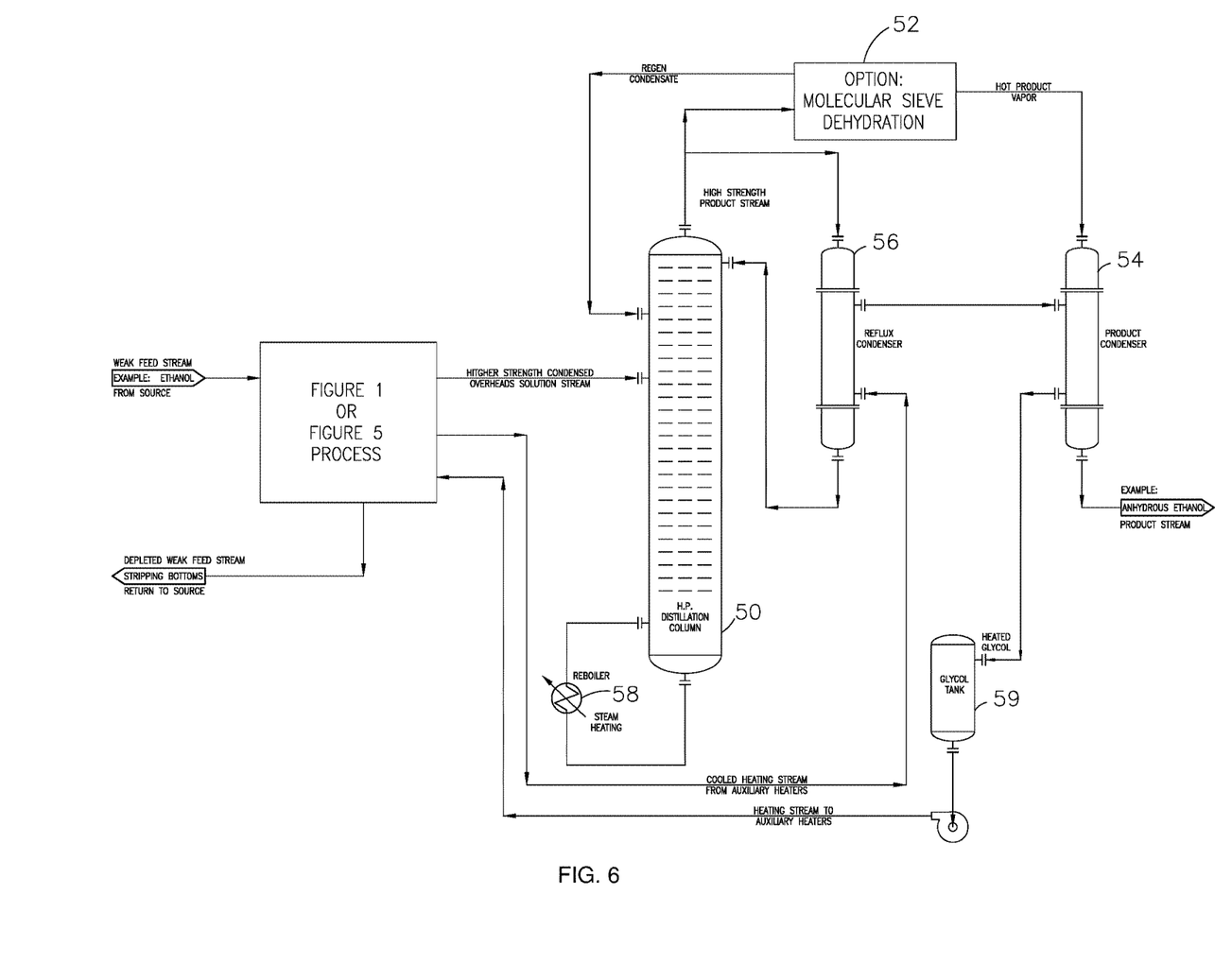
FIG. 6 is a schematic representation of an overall process integration in accordance with an embodiment of the present disclosure.

FIG. 6 shows an example of heat integration providing the heat to the auxiliary heaters of FIGS. 1 and 5. As outlined in the description of FIGS. 1 and 5, which are examples of the disclosure presented, a weak ethanol feed stream is processed to produce a stronger ethanol product stream, for example, of from 10 wt % to 30 wt % ethanol depending on the amount of ethanol in the weak stream. This strong ethanol stream is further processed to produce >99 wt % ethanol as a final product stream. The depleted ethanol stream is returned to fermentation or for other upstream processing. FIG. 6 shows the stream interconnections and an embodiment of heat integration using a circulated glycol solution to supply heat to the auxiliary heaters. The strong ethanol stream is distilled in a high pressure distillation column 50 with 88 wt % to 95 wt % ethanol high pressure vapor flowing to a pressure vacuum swing adsorption (PVSA) molecular sieve dehydration system 52. The PVSA 52 returns a water rich regenerate steam back to the high pressure distillation column 50 and hot high pressure ethanol vapor to the ethanol product condenser 54. The high pressure distillation column 50 has a reflux stream of overhead vapor condensing the returning to the top of the column to aid in enriching the overhead vapors in ethanol. A reflux condenser 56 and the ethanol product condenser 54 are cooled with a circulating stream of glycol and water removing the heat of condensing, raising the temperature of the glycol and water stream, returning to a hot glycol tank 59 then pumped to the FIG. 1 or 5 auxiliary heaters to supply supplemental heat and allow only the partial condensing of the FIG. 1 or 5 compressed overhead vapors. Optionally, the heat from the hot product vapor overheads can be directly condensed in the auxiliary heaters. All heat supplied to the high pressure distillation column 50 is from steam supplied to a reboiler 58. A smaller amount of heat is supplied to the PVSA 52 for superheating the vapor feed from the high pressure distillation column 50.

Figure 7:
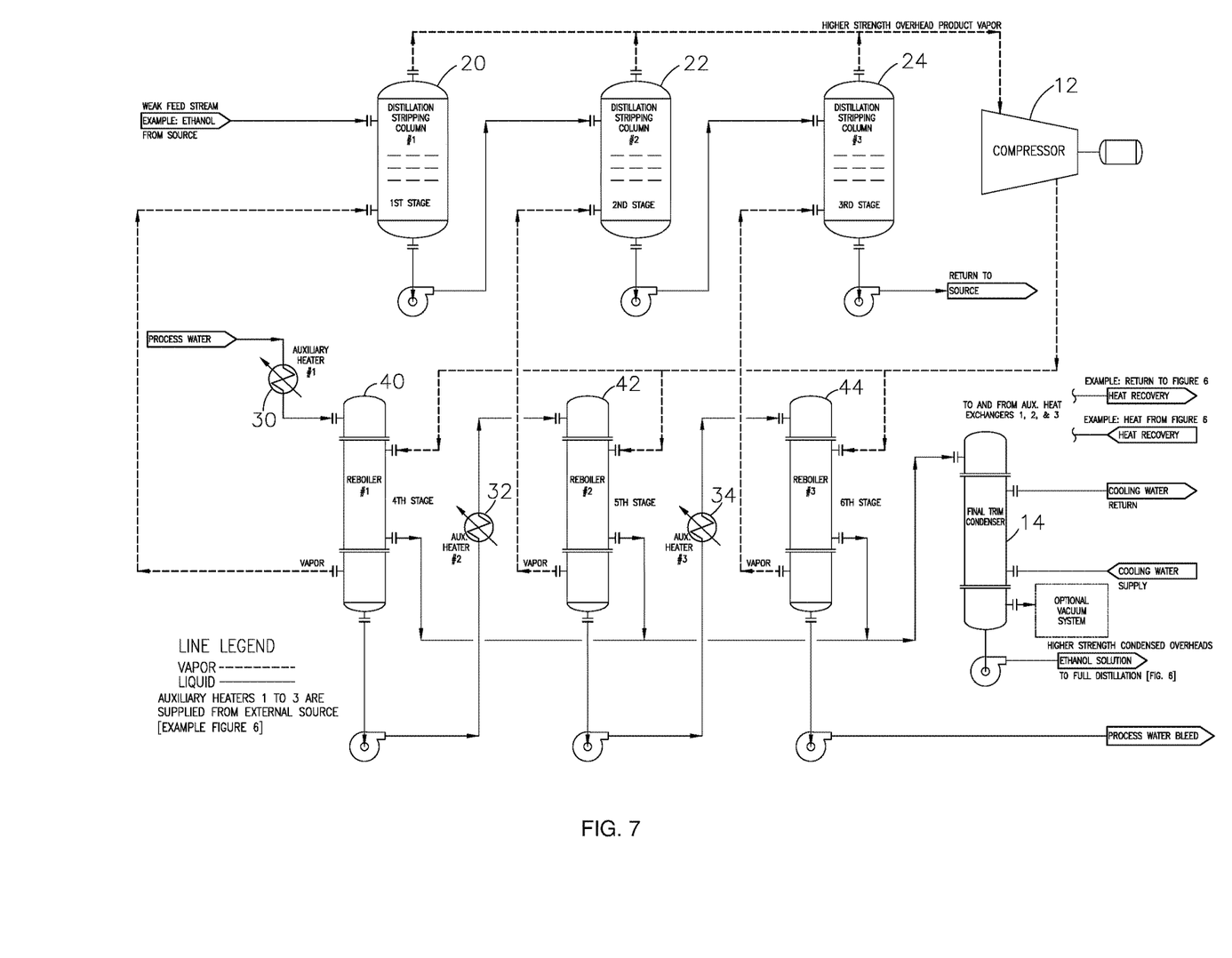
FIG. 7 is a schematic representation of a series liquid and parallel flow concept using process water for reboilers in accordance with an embodiment of the present disclosure.

FIG. 7 shows an embodiment which is a modification of the embodiment shown in FIG. 5 to reduce the exposure of the weak feed stream to a high temperature surface of the reboilers and reduce the residence time in the system of the weak feed stream. A process water stream is fed to the reboilers 40, 42 and 44 to provide a water vapor stream to the bottom of the distillation columns 20, 22 and 24. The weak feed stream flows from the distillation columns 20, 22 and 24 in series reducing the vapor velocity in the columns and flow path of the vapor for lower pressure loss while the weak feed stream depleted of volatile components exits the last stage for return to the source.

Figure 8:
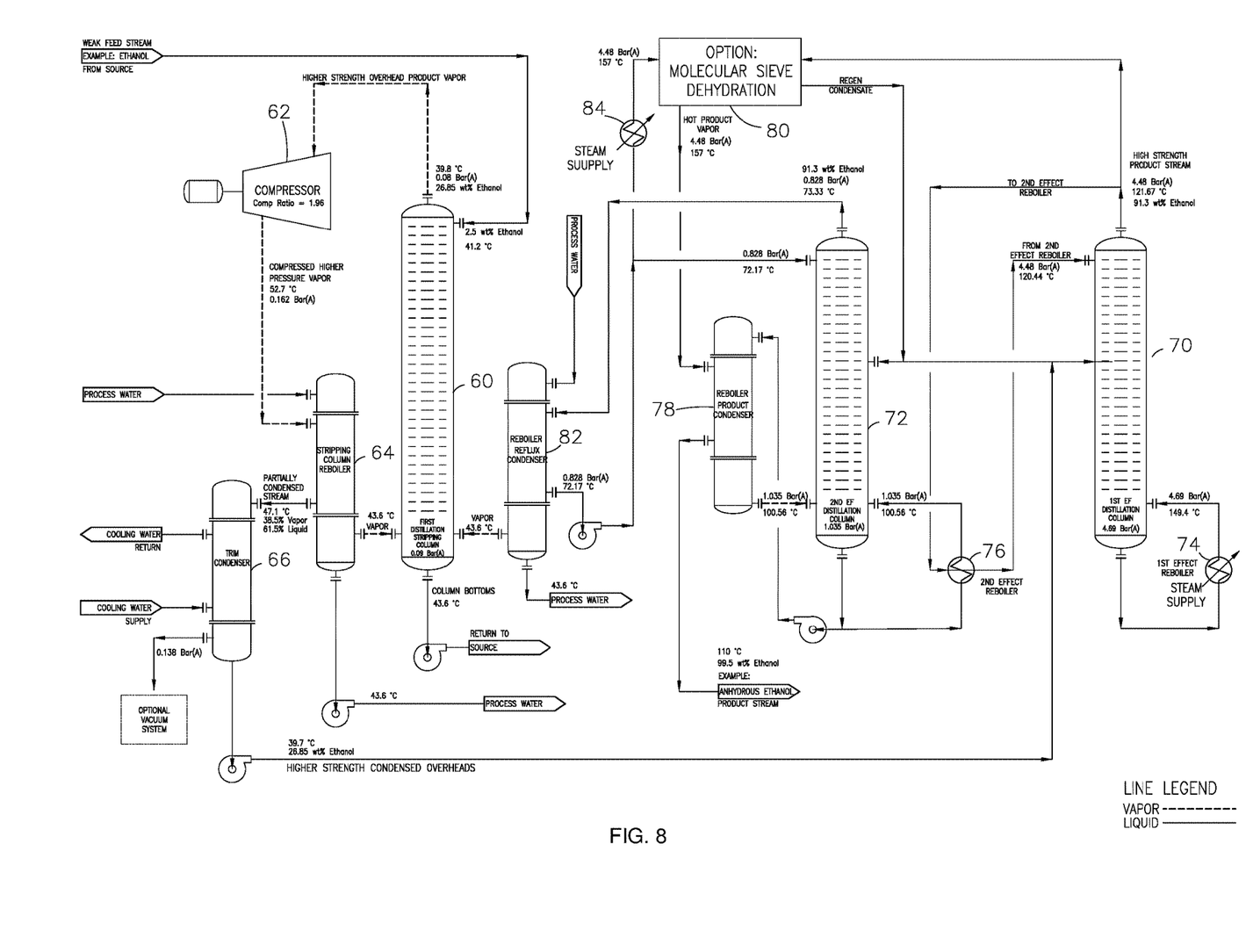
FIG. 8 is a schematic representation of a process sequence in accordance with a preferred embodiment of the present disclosure.

FIG. 8 shows an embodiment of the process sequence wherein the energy required for recovery of ethanol from a weak feed stream in the first distillation stripping column is balanced with that energy required for production of ethanol in a double effect distillation and molecular sieve dehydration system. The overheads of the first distillation stripping column 60 is compressed in a two stage turbofan compressor 62 and partially condensed in a reboiler 64 for the first distillation stripping column 60. Compressed vapor is condensed in the reboiler 64 providing energy for operation of the first distillation stripping column 60. The first distillation stripping column 60 overhead compressed vapor is further condensed in a trim condenser 66 recovering condensate which is pumped to the final higher pressure distillation part of the process. The first distillation stripping column 60 operates at a low temperature and pressure. The final higher pressure part of the process includes first effect distillation column 70 operating at the highest pressure of the overall process system, a second effect distillation column 72 operating at an intermediate pressure between that of the first distillation stripping column 60 and the first effect distillation column 70. A first effect reboiler 74 is heated with steam to operate the first effect distillation column 70 at a sufficient pressure and bottoms temperature. The first effect distillation column 70 overheads high strength product stream is split ⅔ to flow to a $2^{nd}$ effect reboiler 76 and ⅓ to a molecular sieve dehydration system 80. The molecular sieve dehydration system 80 removes water from the high strength product stream forming a stream called the hot product vapor. This is condensed in a third reboiler product condenser 78 for the $2^{nd}$ effect distillation column 72. The overhead vapor from the $2^{nd}$ effect distillation column 72 is condensed in a reboiler reflux condenser 82 of the first distillation stripping column 60 and provides the remaining energy required to operate the first distillation stripping column 80. The condensed vapor in the reboiler reflux condenser 82 is split ⅔ to flow back to the $2^{nd}$ effect distillation column 72 as reflux and ⅓ to flow to a vaporizer/superheater 84 which is steam heated and supplies the molecular sieve dehydration system 80 joining the high strength product stream from the first effect distillation column 70. The combined feeds to the molecular sieve dehydration system 80 forming two product streams from this step called hot product vapor and regen condensate.

In summary energy is supplied to the low pressure first distillation stripping column 60 from recompression of the higher strength overhead product vapor and from condensing the $2^{nd}$ effect distillation column 72 overhead vapor. Primary steam supplies heat to the first effect distillation column reboiler 74 and the vaporizer/superheater 84 of the condensed $2^{nd}$ effect distillation column 72 overheads feeding the molecular sieve dehydration system 80. Energy or heat flows from the first effect distillation column 70 and from hot product vapor of the molecular sieve dehydration 80 to the $2^{nd}$ effect distillation column reboilers 76, 78 then from the $2^{nd}$ effect distillation column 72 to the first distillation stripping column reboiler/reflux condenser 82. The stripping column reboiler 64 partially condenses compressed higher pressure vapor from the compressor 62 recovering condensing heat at a temperature suitable for operation with the lower condensing range temperature which is below useful recovery condensed in the trim condenser 66.

Further in summary weak feed stream from a source is stripped of ethanol in the first distillation stripping column 60 removing ethanol from the source weak feed stream and returning the bottom product to the source. The condensate from the trim condenser 66 forming the higher strength condensed overheads flows to and is split in portions between the first effect distillation column 70 and the $2^{nd}$ effect distillation column 72. Both of these columns produce a high strength product stream (91.3 wt % ethanol in Example 2) and have a bottoms aqueous product of which the ethanol has been removed. The high strength product stream of the first and $2^{nd}$ effect distillation column 72 is dehydrated (water removed) in the molecular sieve dehydration 80 to produce a final anhydrous product stream.

Figure 9:
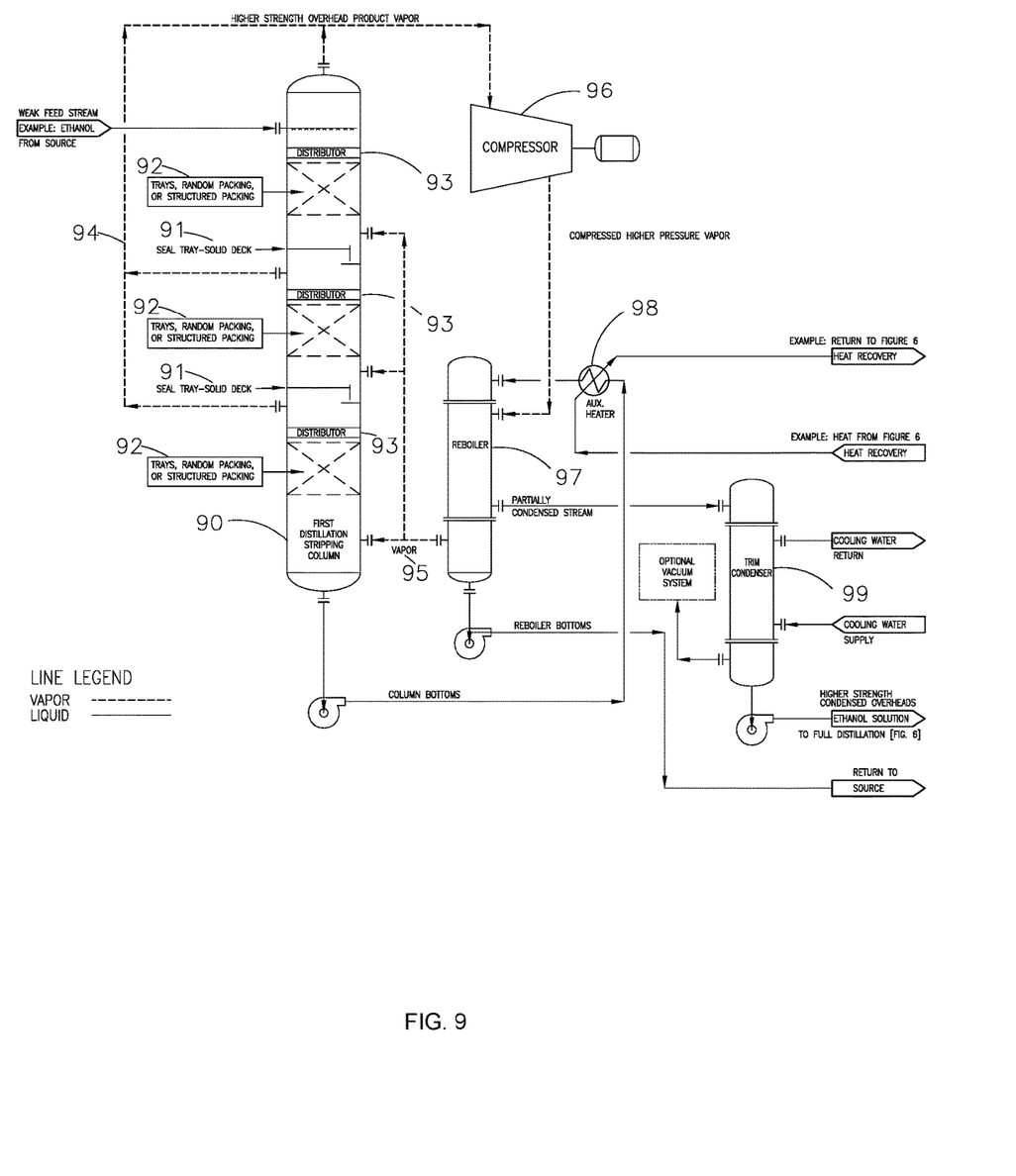
FIG. 9 is a schematic representation of a multi-section column concept in accordance with an embodiment of the present disclosure.

FIG. 9 illustrates an embodiment of a Multi-Section Column concept in one example of its application. The process equipment shown includes a distillation column 90, reboiler 97, compressor 96, trim condenser 99, and an auxiliary heater 98. A weak, for example ethanol, feed stream (can be other low concentration volatile chemical) enters the distillation column 90 divided into a plurality of distributer sections 93, each section having trays, random packing or structured packing 92, separated by seal traysolid decks 91. The weak feed stream source flows down from top to bottom in series through distributer sections 93 while the vapor 95 from the reboiler 4 flows in parallel flow into the bottom and out of the top of each section 93 of the distillation column 90 contacting the liquid at each stage, the action of which sends the more volatile chemical (ethanol) up with the vapor depleting the feed stream of volatile components while increasing the concentration of volatile components in the vapor stream. The overhead vapor exiting the top of the distillation column 90 combines with the flow 94 out each section and flows to a compressor 96 which increases the pressure of the vapor sufficiently above the distillation column 90 pressure that the compressed vapor can be used to heat the reboiler 97. The compressor 96 may be a high speed centrifugal compressor, turbofan, or other gas compression device. The auxiliary heater 98 provides additional heat from an external source to the reboiler 97 by heating the bottom liquid product from the distillation column 90. The reboiler 97 partially condenses the overhead compressed vapor to achieve an economical level of heat recovery. The higher volatile concentration of the compressed vapor condenses in the reboiler 97 providing heat to the reboiler 97 by release of the vapor's latent heat. Optionally, the single reboiler can be replaced by a plurality of reboilers for the plurality of distributer sections.

The overall advantage supplied by the integration of the embodiments shown in FIGS. 1, 5, and 6 is an energy input which is less than 15% of that required for a single distillation recovering 91 wt % ethanol from a 2-3 wt % weak ethanol feed. A similar result can be obtained for weak methanol and other volatile chemicals. This highly energy efficient process is important for the commercial success of advanced bio-economy biomass and renewables processes which deliver in many cases very dilute product streams for further processing.

The disclosure will be further illustrated with reference to the following specific examples. It is understood that these examples are given by way of illustration and are not meant to limit the disclosure or the claims to follow.

Example #1

The source of a weak feed stream is from fermentation of sugars derived from cellulose in which the weak feed stream is 3 wt % ethanol in water with some solids. This weak feed stream is first sent to the first distillation stripping column as shown in FIG. 1. This first distillation stripping column operates with a top pressure of 5 psia. The reboiler and auxiliary heater boil off vapor from the column bottoms and the vapor strips ethanol from the weak feed steam in the first distillation stripping column with most of the ethanol leaving the column as 28 wt % ethanol/72 wt % water vapor in the higher strength overhead product vapor. The overhead product vapor is compressed to 9.8 psia in the compressor. The bottom pressure and temperature of the first distillation stripping column is 6 psia and 170° F. The compressed overhead product first condenses at 186.2° F. and is fully condensed at 166° F. For this reason the reboiler of FIG. 1 only condenses the compressed overhead product vapor partially to 178.2° F. which is 62.2% of the available heat from condensing the vapor. The trim condenser of FIG. 1 completes the condensation of the overhead vapor.

An auxiliary heater supplies the remaining heat required to vaporization of the first distillation stripping column bottoms to fully strip ethanol from the weak feed stream and produce the full amount of vapor in the overheads required for the operation. The heat source for the auxiliary heater comes from distillation and dehydration of the ethanol as shown in FIG. 6. The higher strength condensed overheads solution stream which is the 28 wt % ethanol is sent to a high pressure distillation column operating at 65 psia to produce a high strength product stream of 92 wt % ethanol. The bottom temperature is 298° F. The top temperature of the high pressure column is 250.8° F. with a narrow condensing range. Two thirds of the overhead vapor, high strength product stream from the high pressure column is condensed in the reflux condenser and returned to the top of the column as reflux which is required for the column operation. One third of the overhead vapor is processed in the molecular sieve system to remove the remaining water and produce a 99.5 wt % ethanol product vapor or hot product vapor. This 99.5 wt % product vapor is condensed in the product condenser. Both the product condenser and reflux condenser are of sufficient temperature to heat a recirculating stream of glycol solution. The glycol solution is heated as it flows through the condensers recovering heat from the condensation of the vapors. The high temperature glycol solution heated to 225° F. is pumped to the auxiliary heater of FIG. 1 to provide additional heat for the FIG. 1 reboiler (or for a secondary reboiler). The glycol solution is cooled in the auxiliary heater and returns to the reflux condenser and product condenser to complete the heat exchange loop.

The above described sequence of steps allows heat recovery from further distillation and production of a purified ethanol product while reducing the compression required for the higher strength overhead product vapor of the first distillation stripping column. An overall high energy efficient system such as this then allows the economic recovery of ethanol (and other fuels or chemicals) from sources generating weak solutions.

Optional modifications to Example #1 include:

Using process water in the first distillation stripping column reboiler so that the column bottoms is pumped directly back to the source as shown in FIGS. 7 and 8.

Using multiple distillation stripping columns as shown in FIGS. 5 and 7 so that each column has fewer tray stages and this results in a lower pressure loss in the columns as vapor travels a shorter distance in the column. The total number of tray stages is maintained as the weak feed stream flows in series through the columns and alternately through the reboilers as shown in FIG. 5.

Modifying the single high pressure column shown in FIG. 6 to a series of two columns such as shown in FIG. 8. A higher pressure distillation column, first effect distillation column is heated with steam and its' overhead vapors are condensed in the reboiler of a second lower pressure second effect distillation column. This second column is used to supply heat to the auxiliary heater of FIG. 1. Details of this option are discussed in Example #2.

Example #2

In a preferred embodiment of the inventive process sequence (See FIG. 8) the energy required for recovery of ethanol from a 2.5 wt % weak feed stream in the first distillation stripping column is balanced with that energy required for production of 99.5 wt % ethanol in a double effect distillation and molecular sieve dehydration system. The overheads of the first distillation stripping column at 26.85 wt % ethanol is compressed in a two stage turbofan compression step and partially condensed in the reboiler for the first distillation stripping column. 61.5% of the compressed vapor is condensed in this reboiler providing 70% of the energy required for operation of the first distillation stripping column. The first distillation stripping column overhead compressed vapor is further condensed in a trim condenser recovering a 26.85 wt % ethanol condensate which is pumped to the final higher pressure distillation part of the process. The first distillation stripping column operates at a low temperature and pressure, in this example as shown in FIG. 8, 0.08 Bar(A) overheads and 0.09 Bar(A) bottoms. The final higher pressure part of the process is composed of a first effect distillation column operating at the highest pressure of the overall process system, a second effect distillation column operating at an intermediate pressure between that of the first distillation stripping column and the first effect distillation column. The first effect distillation column reboiler is heated with steam at a pressure sufficient to operate this column at 4.69 Bar(A) (68 psia) and a bottoms temperature of 149.4° C. The first effect distillation column overheads or high strength product steam is composed of 91.3 wt % ethanol at 4.48 Bar(A) (65 psia) and 121.67° C. This vapor stream is split ⅔ to flow to the $2^{nd}$ effect reboiler and ⅓ to the molecular sieve dehydration system. The molecular sieve dehydration removes water from the high strength product stream forming a stream of 99.5 wt % or anhydrous ethanol called the hot product vapor. This is condensed in a second reboiler (reboiler/product condenser) for the $2^{nd}$ effect distillation column. The $2^{nd}$ effect distillation column bottom section operates at 1.035 Bar(A) (15 psia) and 100.56° C. and has an overhead high strength product stream composed of 91.3 wt % ethanol at 0.828 Bar(A) (12 psia) and 73.33° C. The overhead vapor from the $2^{nd}$ effect distillation column is condensed in the reboiler/reflux condenser of the first distillation stripping column and provides the remaining 30% of the energy required to operate the first distillation stripping column. The condensed vapor in the reboiler reflux condenser is split ⅔ to flow back to the $2^{nd}$ effect distillation column as reflux and ⅓ to flow to a vaporizer/superheater which is steam heated and supplies 91.3 wt % ethanol at 4.48 Bar(A) (65 psia) and 157° C. to the molecular sieve dehydration joining the high strength product stream from the first effect distillation column. The combined feeds to the molecular sieve dehydration forming two product streams from this step called hot product vapor and regen condensate.

The above sequence of process steps defines one of the preferred applications of this disclosure. Other alternates to this depend on the source composition and limitations of handling such as fouling tendencies and sensitivity to heat of the source weak feed stream. Other factors such as chemical composition influence the exact configuration of the invention steps. For example for ethanol concentrations higher than 5 wt % a double effect distillation to produce the high strength product stream would be replaced by a single effect/single high pressure column. Another option would be to use an intermediate glycol or thermal fluid circulation loop to transfer heat from the higher temperature portion of the process to the first distillation stripping column auxiliary reboiler/heater. In the case that the source weak feed stream is not heat sensitive the first distillation stripping column would be operated at a much higher temperature and pressure than what is described in the FIG. 8 example. The object in all applications of this disclosure is to provide a low energy consumption to remove ethanol and other volatile chemicals from a weak aqueous feed source by use of a modified mechanical vapor recompression (MVR) to extract a portion of the heat of condensing from the compressed vapor and make use of downstream higher temperature processes for heat recovery to the first distillation stripping column.

The invention claimed is:

1. A method for energy efficient distillation of feed steams of volatile components comprising the steps of:
   (a) providing a feed stream of less than 10 wt% volatile components to a first distillation stripping column;
   (b) distilling the weak feed stream in the first distillation stripping column to form an overhead product vapor stream and directly supplying the overhead product vapor stream to a compressor to produce a compressed vapor;
   (c) partially condensing the compressed vapor in a first distillation stripping column reboiler, partially vaporizing a bottom liquid product from the first distillation stripping column in the first distillation stripping column reboiler and providing a bottom vapor stream to the first distillation stripping column to strip volatile compounds or chemicals from the feed stream;

(d) completing in a trim condenser the condensing of the partially condensed vapor which has been partially condensed in the first distillation stripping column reboiler to recover a condensed overhead stream which is the condensed overhead product vapor stream of the first distillation stripping column;

(e) distilling the condensed overhead product stream in a second distillation column to produce a distilled product stream in the second distillation column overheads; and (f) recovering heat from the second distillation column overheads and adding the recovered heat to the first distillation stripping column reboiler.

2. The method of claim 1 wherein the volatile component is ethanol further comprising reducing by dehydration a moisture content of an ethanol overhead product stream from the second distillation column.

3. The method of claim 2 further comprising recovering heat from the reduced moisture content ethanol stream and adding the recovered heat to the stripping column reboiler.

4. The method of claim 1 wherein the first distillation stripping column is comprised of a series of distillation stripping columns, wherein the first distillation stripping column reboiler is comprised of a series of distillation stripping column reboilers, and a first distillation stripping column in the series receiving the feed stream of volatile components, each of the other distillation stripping columns in the series in succession receiving the bottom stream from the prior distillation stripping column in the series, and each distillation stripping column in the series having a reboiler of the series of reboilers which partially condenses compressed overhead vapor from the series of distillation stripping columns, the reboilers each partially vaporizing the volatile stream from the final distillation stripping column in the series as well as sequentially reducing the volatile components of the feed stream.

5. The method of claim 4 wherein the compressed vapor from the compressor provides a portion of the heating of the series of distillation stripping column reboilers.

6. The method of claim 4 wherein the series of distillation stripping columns comprises one distillation column divided into sections, each section in series flow for the feed stream from top to bottom and in parallel flow for vapor flow into the bottom and out of the top of each section.

7. The method of claim 1 wherein the volatile component of the feed stream contains ethanol as a main volatile constituent.

8. The method of claim 1 wherein the volatile component of the feed stream contains methanol as a main volatile constituent.

9. The method of claim 1 wherein the volatile component of the feed stream contains from 1.0 wt% to 8 wt% ethanol as a main volatile constituent.

10. The method of claim 1 wherein the overhead product vapor stream of the first distillation stripping column is from 10 wt% to 30 wt% ethanol.

11. The method of claim 1 wherein the compressor is a high speed compressor, turbofan, or positive displacement blower.

12. The method of claim 1 wherein the first distillation stripping column comprises multi-pass trays, disc and donut trays, or dumped or structured packing internals.

13. The method of claim 1 wherein the second distillation is a double effect distillation with a primary steam heating the first effect distillation column and the first effect distillation column overheads heating the second effect distillation column while a second effect distillation column overhead vapor heats an auxiliary heater or reboiler of the first distillation stripping column operating at the lowest pressure in the sequence.

14. A method for energy efficient distillation of feed steams of volatile components while limiting the pressure loss in the system by parallel flow of vapor in the distillation operation comprising the steps of:

(a) providing a feed stream of less than 10 wt% volatile components to a series of distillation stripping columns, the first distillation stripping column in the series receiving the feed stream of volatile components, each of the other distillation stripping columns in the series in succession receiving the bottom stream from the prior distillation stripping column in the series, and each distillation stripping column in the series having a reboiler which partially condenses compressed overhead vapor from the series of distillation stripping columns, the reboilers each partially vaporizing a volatile stream from the final distillation stripping column in the series or using an intermediate process water feed as well as sequentially reducing the volatile components of the feed stream while vapor from each of the reboilers flows to the associated distillation stripping column in the series;

(b) distilling the feed stream of volatile components in the series of distillation stripping columns to form an overhead product vapor stream which flows at the same overhead pressure directly supplying a compressor raising the pressure of the overhead vapor to produce a vapor at an operating pressure of a heated side of the reboilers;

(c) partially condensing the vapor in the reboilers, partially vaporizing a bottom liquid product from the series of distillation stripping columns and providing a bottom vapor stream to the associated distillation stripping columns to strip volatile compounds or chemicals from the feed stream;

(d) completing in a trim condenser the condensing of the vapor which has been partially condensed in the reboilers to recover a condensed overhead stream which is the condensed overhead product vapor stream of the series of distillation stripping columns;

(e) distilling the condensed overhead product stream in a second distillation column to produce a product stream in the second distillation column overheads; and (f) recovering heat from the second distillation column overheads and adding the recovered heat to the reboilers.

15. The method of claim 14 wherein the volatile component is ethanol further comprising reducing by dehydration a moisture content of an ethanol overhead product stream from the second distillation column.

16. The method of claim 15 further comprising recovering heat from the reduced moisture content ethanol stream and adding the recovered heat to the reboilers.

17. The method of claim 14 wherein the series of distillation stripping columns comprises one distillation column divided into sections, each section in series flow for the feed stream from top to bottom and in parallel flow for vapor flow into the bottom and out of the top of each section.

18. The method of claim 14 wherein the volatile component of the feed stream contains ethanol as a main volatile constituent.

19. The method of claim 14 wherein the volatile component of the feed stream contains methanol as a main volatile constituent.

20. The method of claim 14 wherein the volatile component of the feed stream contains from 1.0 wt% to 8 wt% ethanol as a main volatile constituent.

21. The method of claim 14 wherein the product stream overhead vapor of the series of distillation stripping columns is from 10 wt% to 30 wt% ethanol.

22. The method of claim 14 wherein the compressor is a high speed compressor, turbofan, or positive displacement blower.

23. The method of claim 14 wherein the series of distillation stripping columns comprise a multi-pass tray, disc and donut trays, or dumped or structured packing internals.

24. The method of claim 14 wherein the second distillation is a double effect distillation with a primary steam heating the first effect distillation column and the first effect distillation column overheads heating the second effect distillation column while a second effect distillation column overhead vapor heats an auxiliary heater or reboiler of the first distillation stripping column operating at the lowest pressure in the sequence.

25. A method for processing a feed stream, comprising:
stripping a feed stream of less than 10 wt% volatile components in a first stripping column forming an overhead vapor;
compressing the overhead vapor in a compression step to produce a compressed vapor;
partially condensing the compressed vapor in a first stripping column reboiler;
further condensing the partially condensed vapor in a trim condenser to form a condensate;
distilling the condensate from the trim condenser in a distillation system;
and providing heat from the condensate distillation to an auxiliary heater or reboiler of the first stripping column.

* * * * *